United States Patent
Adamson et al.

(10) Patent No.: US 12,171,523 B2
(45) Date of Patent: Dec. 24, 2024

(54) EAR IMAGING SYSTEM

(71) Applicant: AUDIOPTICS MEDICAL INC., Halifax (CA)

(72) Inventors: Robert B. A. Adamson, Halifax (CA); Matthew Jahns, Halifax (CA); Daniel MacDougall, Dartmouth (CA); Joshua Farrell, Halifax (CA); Matthew Farrell, Halifax (CA); Drew Hubley, Halifax (CA)

(73) Assignee: AUDIOPTICS MEDICAL INC., Halifax (CA)

( * ) Notice: Subject to any disclaimer, the term of this patent is extended or adjusted under 35 U.S.C. 154(b) by 589 days.

(21) Appl. No.: 17/442,996

(22) PCT Filed: Mar. 25, 2020

(86) PCT No.: PCT/CA2020/050391
§ 371 (c)(1),
(2) Date: Sep. 24, 2021

(87) PCT Pub. No.: WO2020/191492
PCT Pub. Date: Oct. 1, 2020

(65) Prior Publication Data
US 2022/0167881 A1    Jun. 2, 2022

Related U.S. Application Data

(60) Provisional application No. 62/823,432, filed on Mar. 25, 2019.

(51) Int. Cl.
*A61B 5/00*    (2006.01)
*A61B 1/00*    (2006.01)
(Continued)

(52) U.S. Cl.
CPC ............ *A61B 5/0066* (2013.01); *A61B 1/046* (2022.02); *A61B 1/227* (2013.01); *A61B 5/0002* (2013.01);
(Continued)

(58) Field of Classification Search
CPC ..... A61B 1/00009; A61B 1/046; A61B 1/227; A61B 5/0002; A61B 5/0051; A61B 5/0066; A61B 5/123; A61B 5/742; A61B 5/7475
See application file for complete search history.

(56) References Cited

U.S. PATENT DOCUMENTS

| | | | |
|---|---|---|---|
| 5,363,839 A | 11/1994 | Lankford | |
| 5,919,130 A | 7/1999 | Monroe et al. | |

(Continued)

FOREIGN PATENT DOCUMENTS

| | | |
|---|---|---|
| WO | 2012118958 A2 | 9/2012 |
| WO | 2016205760 A1 | 12/2016 |
| WO | 2018152632 A1 | 8/2018 |

OTHER PUBLICATIONS

Pitris, C. et al., "High-Resolution Imaging of the Middle Ear With Optical Coherence Tomography", Arch Oto.-Head Neck Surg. 127, 637-642, 2001.
(Continued)

*Primary Examiner* — Amelie R Davis
(74) *Attorney, Agent, or Firm* — NIXON PEABODY LLP; Jeffrey L. Costellia; Kevin R. Gualano

(57) ABSTRACT

Systems and methods are described for performing diagnostic procedures, such as vibrometric diagnostic procedures. An example system includes a handheld vibrometric device, a handheld controller, and a control and processing console. The handheld controller includes an input receiving mechanism for controlling the handheld vibrometric device and/or
(Continued)

controlling a user interface generated by the console. The handheld controller is configured such that when the handheld vibrometric diagnostic device is supported by a first hand of an operator and the handheld controller is supported by a second hand of the operator, the input receiving mechanism is capable of being actuated by a digit of the second hand while maintaining support of the handheld controller by the second hand, in the absence of contact with the control and processing console and the handheld vibrometric diagnostic device, thereby facilitating control of the handheld vibrometric diagnostic device without mechanically perturbing the handheld vibrometric diagnostic device.

22 Claims, 16 Drawing Sheets

(51) Int. Cl.
*A61B 1/04* (2006.01)
*A61B 1/227* (2006.01)
*A61B 5/12* (2006.01)

(52) U.S. Cl.
CPC .............. *A61B 5/123* (2013.01); *A61B 5/742* (2013.01); *A61B 5/7475* (2013.01); *A61B 1/00009* (2013.01)

(56) References Cited

U.S. PATENT DOCUMENTS

| | | |
|---|---|---|
| 8,115,934 B2 | 2/2012 | Boppart et al. |
| 8,594,757 B2 | 11/2013 | Boppart et al. |
| 10,682,058 B2 | 6/2020 | Koch et al. |
| 10,687,738 B2 | 6/2020 | MacDougall et al. |
| 10,729,327 B2 | 8/2020 | Adamson et al. |
| 2020/0315499 A1 | 10/2020 | Adamson et al. |

OTHER PUBLICATIONS

International Search Report for PCT/CA2020/050391 dated Jul. 22, 2020.

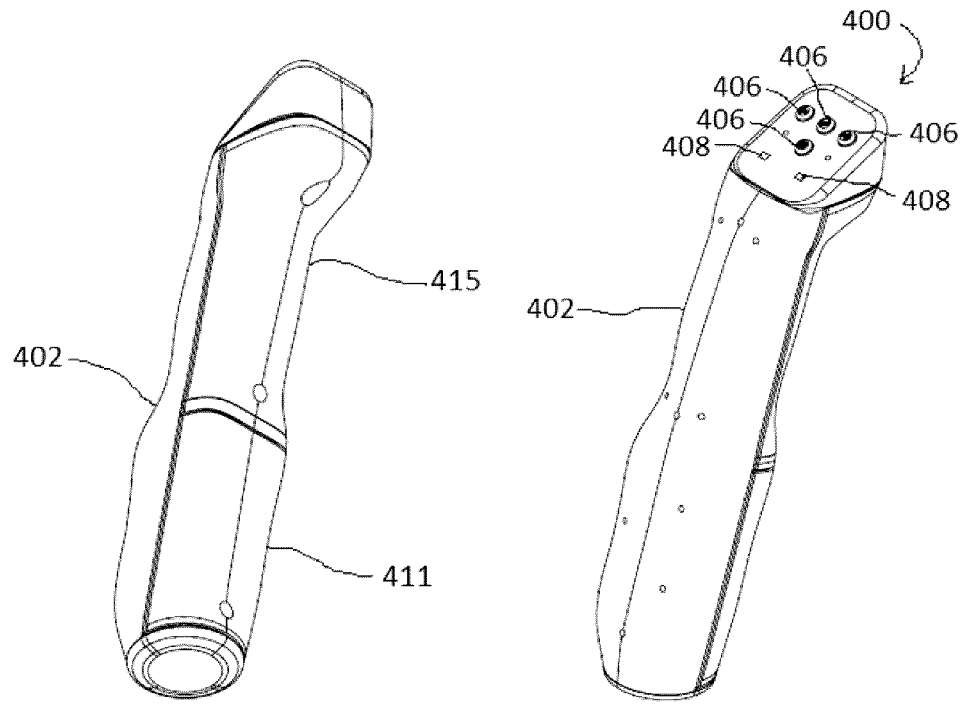
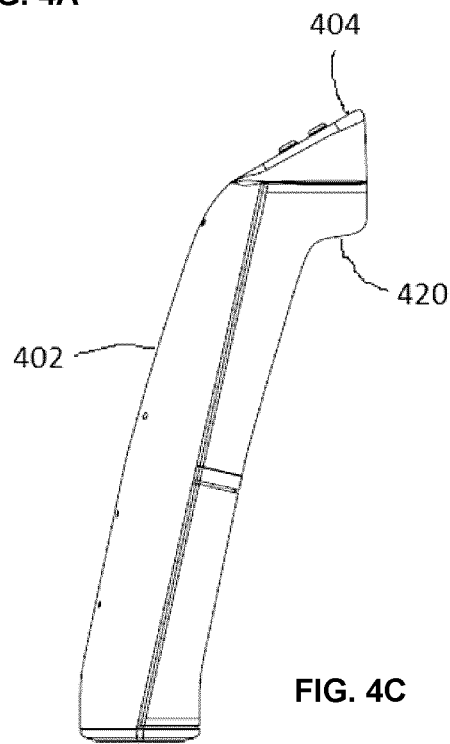
FIG. 4A
FIG. 4B
FIG. 4C

EAR IMAGING SYSTEM

CROSS-REFERENCE TO RELATED APPLICATION

This application is a National Phase application claiming the benefit of the International PCT Patent Application No. PCT/CA2020/050391, filed on Mar. 25, 2020, in English, which claims priority to U.S. Provisional Patent Application No. 62/823,432, titled "EAR IMAGING SYSTEM" and filed on Mar. 25, 2019, the entire contents of which are incorporated herein by reference.

BACKGROUND

The present disclosure relates to handheld diagnostic devices and methods of use thereof. In some aspects, the present disclosure relates to devices and methods for vibrometric assessment and imaging of the ear.

Conductive hearing loss has a 7% prevalence in the adult population and affects roughly 420 M people worldwide. Conductive hearing loss is typically caused by a failure of the middle ear—the tympanic membrane and ossicular chain—to effectively conduct sound from the ear canal to the cochlea. This failure in middle ear function may be due to fixation, caused by, for example, the ingrowth of soft tissues or adhesions, stiffening of ossicular joints, the formation of plaque on the stapes footplate, congenital malformation etc. or to discontinuity in the ossicular chain due, for example, to erosion of the ossicles, traumatic injury or congenital defects. Conductive hearing loss may also be caused by perforation or sclerosis of the tympanic membrane, middle ear fluid or a number of less common reasons. For many of these disorders there are a number of surgical interventions that may be undertaken in order to restore hearing. These include, for instance, inserting drainage tubes in the tympanic membrane, replacement of ossicles with prostheses and procedures to close off tympanic membrane perforations. In order to select the correct intervention and to be able to inform patients about their treatment options, ear specialists have a need to be able to obtain accurate ear diagnoses in the clinic prior to performing surgery.

Ear specialists have a number of diagnostic tools available to them. Audiometry can distinguish conductive hearing loss from the more common sensorineural hearing loss by the presence of an Air-Bone Gap in the audiogram. Tympanometry can identify abnormal eardrum stiffness or compliance that may be indicative, respectively, of a fixation or discontinuity. Computed tomography and magnetic resonance imaging are non-invasive imaging modalities that are sometimes used to image the middle ear. Microscopic examination of the eardrum can help to assess the state of the tympanic membrane and can sometimes provide information about the middle ear, although the opacity of the eardrum prevents the middle ear from being clearly imaged through simple microscopy.

An otoscope is a specialized microscope for visualizing the tympanic membrane that includes a handle, a disposable plastic speculum, an illumination source, and an imaging head containing imaging optics. Clinicians hold otoscopes in a variety of ways depending on their training, usually with their dominant hand. Some clinicians hold the otoscope by the handle, while others pinch the otoscope near the speculum holder between the fingers and point the handle up and in the superior-anterior or superior-posterior directions. Some clinicians will brace their hand against the patient by placing a finger (e.g., an index or pinky finger) on the patient's face (e.g., on the cheek or behind the pinna) in order to stabilize the imaging head in the ear, respond quickly to patient motion, and control the depth of insertion of the speculum. The non-dominant hand is then used to pinch and pull back on the patient's pinna, which tends to straighten the ear canal, permitting a clearer view of the tympanic membrane. Once the speculum is inserted into the ear canal, the speculum may hold the ear canal straight and the pinna can then be released.

Recently, video otoscopes have become common, examples of which are described in U.S. Pat. Nos. 5,363,839 and 5,919,130. These devices have the form factor of a traditional otoscope but contain a digital camera that can take pictures of the tympanic membrane. There has been interest in the use of optical coherence tomography as a tool for visualizing the structures of the middle ear. Optical coherence tomography (OCT) is an interferometric optical imaging modality that uses light to produce depth-resolved images similar in appearance to ultrasound images. OCT is able to see through the tympanic membrane to visualize the structures in the middle ear. In addition, phase-sensitive OCT imaging or "Doppler OCT" can be used to measure the response of ear structures to sound, a feature that can help clinicians in localizing functional defects like fixations and discontinuities, examples of which are described in Pitris, C. et al., "High-resolution imaging of the middle ear with optical coherence tomography: A feasibility study," Arch Otolaryngol Head Neck Surg., 127, pp. 637-642, (2001); U.S. Pat. No. 8,115,934; and U.S. Patent Publication No. 2017/0251924.

Some video otoscopes have a simple user interface mounted along the imaging screen and/or along the top or sides of the imaging head. However, it is awkward for the user to operate buttons located on the imaging head with the same hand used to hold the otoscope in the ear. Further, because obtaining high quality images requires that the imaging device remain still throughout imaging, placing buttons on the imaging device tends to degrade image quality as pressing the buttons causes device motion. Some medical devices, not necessarily video otoscopes, that require handheld operation use foot pedals for user input. Others rely on a second operator to operate a console or computer terminal in order to interact with the tool. These, too, have disadvantages from an ease-of-use or practicality perspective.

While OCT has been widely used for imaging the eye, particularly the retina, the use of OCT for imaging the ear is relatively new. Because ear specialists are familiar with the otoscope form factor and because it is known to be able to be held in a way that provides clear images of the tympanic membrane, most ear OCT devices are built with an otoscopic form factor for the dominant hand. The non-dominant hand is typically left available for manipulation of the pinna and OCT images are displayed on a screen viewable by the clinician.

The power and variety of techniques achievable with OCT makes existing medical device interfaces very cumbersome, however, since reaching to manipulate controls on an imaging screen, console, along the imaging head, or stepping upon foot pedals would disturb the normal ergonomic practice of the ear specialist and limits the uptake of new OCT systems and the clinical applications thereof. None of the input methods or user interfaces currently in use are truly effective for these clinicians. There remains a need to devise improved user interfaces that can provide the clinician with intuitive control of OCT ear imaging systems compatible within the various otoscope handling practices in clinical use.

SUMMARY

Systems and methods are described for performing diagnostic procedures, such as vibrometric diagnostic procedures. An example system includes a handheld vibrometric device, a handheld controller, and a control and processing console. The handheld controller includes an input receiving mechanism for controlling the handheld vibrometric device and/or controlling a user interface generated by the console. The handheld controller is configured such that when the handheld vibrometric diagnostic device is supported by a first hand of an operator and the handheld controller is supported by a second hand of the operator, the input receiving mechanism is capable of being actuated by a digit of the second hand while maintaining support of the handheld controller by the second hand, in the absence of contact with the control and processing console and the handheld vibrometric diagnostic device, thereby facilitating control of the handheld vibrometric diagnostic device without mechanically perturbing the handheld vibrometric diagnostic device.

Accordingly, in one aspect, there is provided a vibrometric diagnostic system for imaging within an ear of a subject, the vibrometric diagnostic system comprising:
  a handheld vibrometric diagnostic device comprising a distal region configured for insertion within the ear of the subject during a diagnostic procedure;
  a control and processing console operatively connected to the handheld vibrometric diagnostic device, the control and processing console comprising at least one processor and associated memory, the memory comprising instructions executable by the processor for performing operations comprising:
    sending control signals to the handheld vibrometric diagnostic device for controlling operations thereof;
    processing vibrometric data received from the handheld vibrometric diagnostic device; and
  a handheld controller operatively connected to the control and processing console, the handheld controller comprising:
    an input receiving mechanism; and
    control circuitry for communicating an input signal associated with actuation of the input receiving mechanism to the control and processing console for use in controlling operation of the handheld vibrometric diagnostic device, such that the control signals are dependent on the input signal;
  the handheld controller being configured such that when the handheld vibrometric diagnostic device is supported by a first hand of an operator and the handheld controller is supported by a second hand of the operator, the input receiving mechanism is capable of being actuated by a digit of the second hand while maintaining support of the handheld controller by the second hand, in the absence of contact with the control and processing console and the handheld vibrometric diagnostic device, thereby facilitating control of the handheld vibrometric diagnostic device without mechanically perturbing the handheld vibrometric diagnostic device.

In some implementations of the system, the handheld controller comprises a support configured to contact the second hand during use for at least partially supporting a weight of the handheld controller while permitting use of at least two digits of the second hand. The support may comprise a support surface positioned to contact an upper portion of the second hand of the operator during use of the handheld controller, such that at least a portion of the weight of the handheld controller is supported. The support may comprise a strap configured to support the handheld controller relative to the second hand. The support may comprise one or more rings, each ring being configured to receive a respective digit of the second hand. The support may comprise at least a portion of a glove that is integrated with the handheld controller for supporting the handheld controller while permitting use of the at least two digits.

In some implementations of the system the processor is further configured to display, on a display device, in real-time while the handheld vibrometric diagnostic device resides in an operative position with the distal region residing within the ear of the subject, a user interface comprising one or more vibrometric measures; wherein the input receiving mechanism is further configured for receiving input from the operator for controlling the user interface while maintaining support of the handheld controller by the second hand, in the absence of contact with the control and processing console and the handheld vibrometric diagnostic device, thereby facilitating control of the user interface without mechanically perturbing the handheld vibrometric diagnostic device.

In some implementations of the system, the handheld controller comprises a wireless transmitter for transmitting the input signal to the control and processing console, such that the handheld controller is absent of a physical connection to the control and processing console, thereby avoiding transmission of mechanical vibrations to the handheld vibrometric diagnostic device via the control and processing console during the diagnostic procedure.

In some implementations of the system, the handheld vibrometric diagnostic device employs an optical imaging modality. The optical imaging modality may be optical coherence tomography. The handheld vibrometric diagnostic device may further comprise a camera and a light source configured to collect image data in one or more of an infrared and visible spectrum.

In some implementations of the system, the handheld vibrometric diagnostic device and the handheld controller are shaped so as to be interchangeable with respect to which hand the operator employs to hold either device.

In another aspect, there is provided an ear imaging system for use by an operator for imaging an ear of a subject, the ear imaging system comprising:
  a handheld imaging device; and
  a stabilization rod emanating from the handheld imaging device, the stabilization rod comprising a terminal element suitable for placement against a head of the subject for stabilization of the handheld imaging device against motion of the subject during an imaging procedure.

In some aspects of the system, the stabilization rod is capable of telescoping motion. The stabilization rod may be mounted so as to emanate from the handheld imaging device at a screw mount attached to a housing of the handheld imaging device. The handheld imaging device may comprise a speculum, wherein the screw mount is midline above the speculum. The system may further comprise one or more additional screw mounts, each screw mount being configured for extending the stabilization rod at a different offset relative to the handheld imaging device housing.

In another aspect, there is provided a system for performing a medical procedure on a subject, the system comprising:
- a handheld medical device comprising a distal region configured for insertion within the subject during the medical procedure;
- a control and processing console operatively connected to the handheld medical device, the control and processing console comprising at least one processor and associated memory, the memory comprising instructions executable by the processor for sending control signals to the handheld medical device for controlling operations thereof;
- a handheld controller operatively connected to the control and processing console, the handheld controller comprising:
  - an input receiving mechanism; and
  - control circuitry for communicating an input signal associated with actuation of the input receiving mechanism to the control and processing console for use in controlling of operation of the handheld medical device, such that the control signals are dependent on the input signal;
- the handheld controller being configured such that when the handheld medical device is supported by a first hand of an operator and the handheld controller is supported by a second hand of the operator, the input receiving mechanism is capable of being actuated by a digit of the second hand while maintaining support of the handheld controller by the second hand, in the absence of contact with the control and processing console and the handheld medical device, thereby facilitating control of the handheld medical device without mechanically perturbing the handheld medical device.

In some aspects of the system, the handheld medical device is a handheld therapeutic device. The handheld controller may comprise a support configured to contact the second hand during use for at least partially supporting a weight of the handheld controller while permitting use of at least two digits of the second hand.

In another aspect, there is provided an imaging system for imaging within an ear of a subject, the imaging system comprising:
- a handheld imaging device comprising a distal region configured for insertion within the ear of the subject during an imaging procedure;
- a control and processing console operatively connected to the handheld imaging device, the control and processing console comprising at least one processor and associated memory, the memory comprising instructions executable by the processor for performing operations comprising:
  - sending control signals to the handheld imaging device for controlling operations thereof;
  - processing image data received from the handheld imaging device to generate an image; and
- a handheld controller operatively connected to the control and processing console, the handheld controller comprising:
  - an input receiving mechanism; and
  - control circuitry for communicating an input signal associated with actuation of the input receiving mechanism to the control and processing console for use in controlling operation of the handheld imaging device, such that the control signals are dependent on the input signal;
- the handheld controller being configured such that when the handheld imaging device is supported by a first hand of an operator and the handheld controller is supported by a second hand of the operator, the input receiving mechanism is capable of being actuated by a digit of the second hand while maintaining support of the handheld controller by the second hand, in the absence of contact with the control and processing console and the handheld imaging device, thereby facilitating control of the handheld imaging device without mechanically perturbing the handheld imaging device.

In another aspect, there is provided an imaging system for imaging within an ear of a subject, the imaging system comprising:
- a handheld imaging device comprising a distal region configured for insertion within the ear of the subject during an imaging procedure;
- a control and processing console operatively connected to the handheld imaging device, the control and processing console comprising at least one processor and associated memory, the memory comprising instructions executable by the processor for performing operations comprising:
  - processing image data received from the handheld imaging device to generate an image; and
  - display, on a display device, in real-time while the handheld imaging device resides in an operative position with the distal region residing within the ear of the subject, a user interface comprising the image; and
- a handheld controller operatively connected to the control and processing console, the handheld controller comprising:
  - an input receiving mechanism; and
  - control circuitry for communicating an input signal associated with actuation of the input receiving mechanism to the control and processing console for use in controlling operation of the user interface;
- the handheld controller being configured such that when the handheld imaging device is supported by a first hand of an operator and the handheld controller is supported by a second hand of the operator, the input receiving mechanism is capable of being actuated by a digit of the second hand while maintaining support of the handheld controller by the second hand, in the absence of contact with the control and processing console and the handheld imaging device, thereby facilitating control of the user interface without mechanically perturbing the handheld imaging device.

In another aspect, there is provided a method of performing a diagnostic procedure involving an ear of a subject, the method comprising:
- providing a system as described above, wherein the handheld medical device is a handheld diagnostic device and wherein the distal region of the handheld diagnostic device is configured for insertion into the ear;
- while supporting the handheld diagnostic device with the first hand and supporting the handheld controller with the second hand:
  - employing at least two digits of the second hand to grip and pull back on a pinna of the ear of the subject; and
  - inserting the distal region of the handheld diagnostic device into the ear of the subject; and
  - without contacting the handheld diagnostic device with the second hand, employing one or more digits of the second hand to actuate the input receiving mechanism to initiate a diagnostic measurement with the handheld diagnostic device.

In some aspects of the method, the pinna is gripped by knuckles of two interior fingers of the second hand.

In some aspects of the method, the pinna is gripped by a thumb and an interior finger of the second hand.

In some aspects of the method the input receiving mechanism is actuated by a thumb.

In an aspect, a clinical imaging remote controller for use by a first person and usable in conjunction with an imaging system is provided. The controller has a controller housing, a top surface, and a transmitter, the housing being shaped so as to allow for the first person to hold the controller without the use of distal phalanges on the hand's non-thumb digits. The controller housing's top surface includes at least one depressible button, disposed upon the top surface such that the thumb on the first person's hand is able to depress and operate the depressible button while the first person holds the controller. The transmitter transmits information to the imaging system as to when the at least one button is activated.

Implementations may include one or more of the following. The controller housing also has a support ledge substantially opposite to the top surface, wherein the first person's hand may support the controllers weight by contact with the support ledge. The controller's housing is so shaped as to allow for the first person's hand to simultaneously and one-handedly hold the controller housing and depress the button with a thumb, optionally while gripping a second person's pinna using the hand's distal phalanges. The controller is so shaped as to allow for the first person's hand to support the controller's weight by contact with the support ledge, while using knuckles of two interior fingers to grip and, optionally, pull back on the pinna, wherein the thumb is free to interact with buttons. The controller is so shaped as to allow for the first person's hand to support the controller's weight by contact with the support ledge, while using the thumb and an interior finger to grip and, optionally, pull back on the pinna. There are at least four depressible buttons disposed on the top surface arranged in a T shape upon the top surface. There is at least one light indicator. There are at least two light indicators. The indicators are light emitting diodes. The controller has a battery compartment and the housing has a lid for access to the battery compartment. There is a battery in the compartment. The controller has a circuit board compartment that contains a printed circuit board and the housing has a circuit board compartment lid for access to the circuit board compartment. The circuit board electrically connects to the battery via the battery compartment, to the transmitter, and to the at least one button.

In an aspect, an ear imaging system for use by a user imaging an ear of a subject is provided. The system has a handheld remote controller as described above and a handheld imaging device, both for use with a computer equipped with a display and receiving hardware for the information provided by the controller's transmitter; in which the computer is programmed to display information relevant to operation of the handheld imaging device based on input received from the controller. Implementations may include one or more of the following. The imaging device is an optical coherence tomography imaging device for imaging of tympanic membrane and middle ear, and it has a speculum insertable into the subject's ear canal. The imaging device also has a camera and a light source, wherein the imaging device also images the tympanic membrane and middle ear in the visible or infrared spectrum. The handheld imaging device has a housing so shaped as to allow for a user to hold in one hand while the remote controller is held in the users other hand. The device housing and controller housing are shaped so as to be interchangeable with respect to which hand the user chooses to use to hold either device. The handheld imaging device also has a stabilization rod emanating from the device wherein the rod has a terminal element suitable for placement against the subject's head for stabilization against subject motion during imaging. The rod is capable of telescoping motion when telescoped by the user. The rod is mounted so as to emanate from the device at a screw mount attached to the handheld imaging device housing. The screw mount is midline above the speculum. A plurality of screw mounts is attached to the handheld imaging device housing.

These and other features and aspects, and combinations of them, may be expressed as methods, systems, components, means and steps for performing functions, apparatus, articles of manufacture, compositions of matter, and in other ways.

Among other advantages, a remote handheld controller as described herein can be used in one hand of a clinician in conjunction with a remote handheld imaging device in the other hand of the clinician, to acquire, refine, analyze, and record OCT and infrared images of the tympanic membrane and middle ear of a patient. Other advantages and features will become apparent from the following description and claims.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 4A-4C show the exterior of a handheld remote controller in various plan and perspective views.

DETAILED DESCRIPTION

Figure 1A:
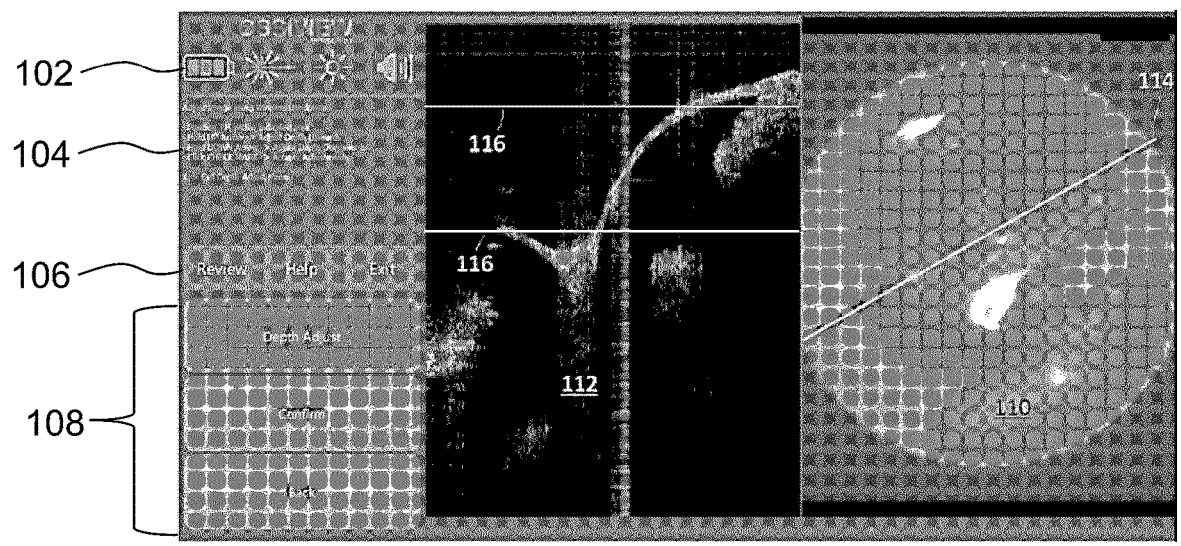
FIG. 1A shows a window on a computer display for an ear imaging system in brightness mode (B-mode), with the diagonal line across the infrared image illustrating the slice selected for showing in B-mode and the upper and lower horizontal lines across the B-mode image illustrating the depth selected.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Historically, ear imaging devices such as video endoscopes had a user interface that was controlled at a monitor console. To adjust imaging settings, either a second user had to press buttons on the console or the single user would have to alternately manipulate the console and image the ear. These historical interfaces are awkward.

An important difference with OCT ear imaging systems and devices as compared to traditional otoscopes and video otoscopes, is that the range of available features and functions is much greater. While a video otoscope is limited to taking pictures or video of the ear drum, in some embodiments a middle ear OCT system can do one or more of capturing still otoscopic images, capturing otoscopic video, capturing B-mode images, capturing B-mode video, selecting B-mode slices within the middle ear volume, selecting slice orientation within the middle ear volume, performing volumetric data acquisitions, rendering and displaying 3D data, rotating, panning and zooming through 3D data, selecting a frequency of sound stimulus, selecting a duration of sound stimulus, selecting a line in the volume for Doppler OCT, initiating the capture of Doppler OCT data, initiating a sound stimulus, reviewing recorded data, and entering patient information. Example displays for a user interface are shown in FIGS. 1A and 1B.

In FIG. 1A, a window 100 on a computer display for an ear imaging system in B-mode displays status indicators 102, user instructions 104, program menu 106, and mode command buttons 108. An infrared camera image 110 displaying the tympanic membrane and middle ear of a subject has an overlaid diagonal line 114 across the infrared image that illustrates the slice selected for showing in B-mode. The B-mode image 112 is overlaid with depth selection indicators 116 as upper and lower horizontal lines across the B-mode image, illustrating the depth selected for imaging.

Figure 1B:
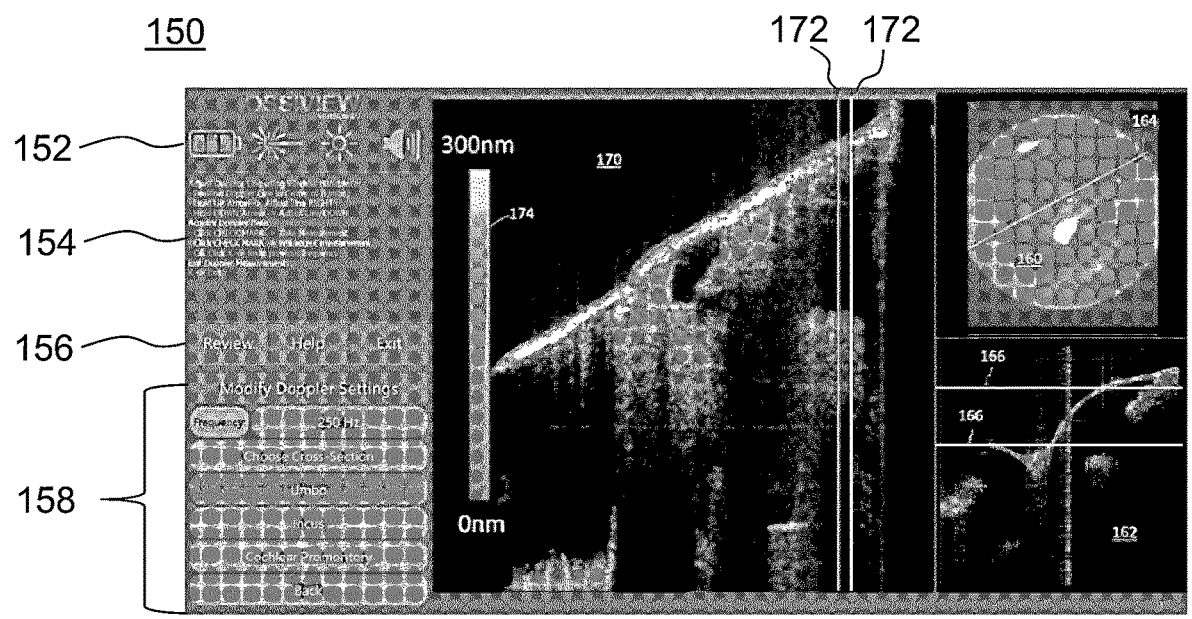
FIG. 1B shows a window on a computer display for Doppler imaging mode, with left and right vertical lines containing a region with vibration displacement amplitude information in false color.
Figure 2A:
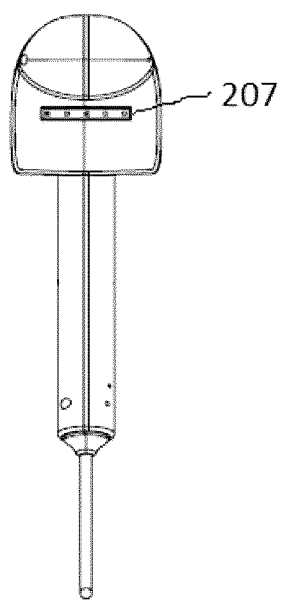
FIGS. 2A-2D show the exterior of a handheld OCT ear imaging device in various plan and perspective views.
Figure 2B:
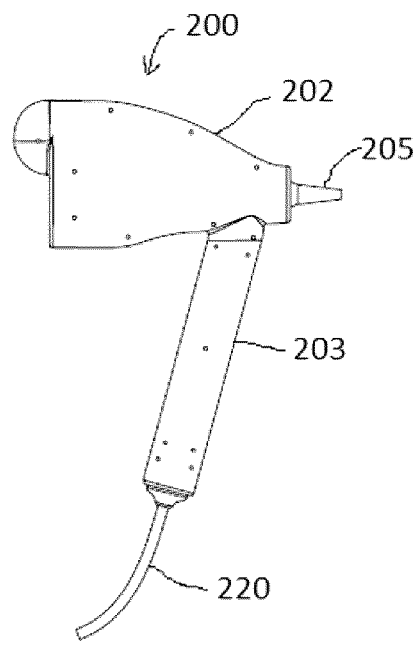
Figure 2C:
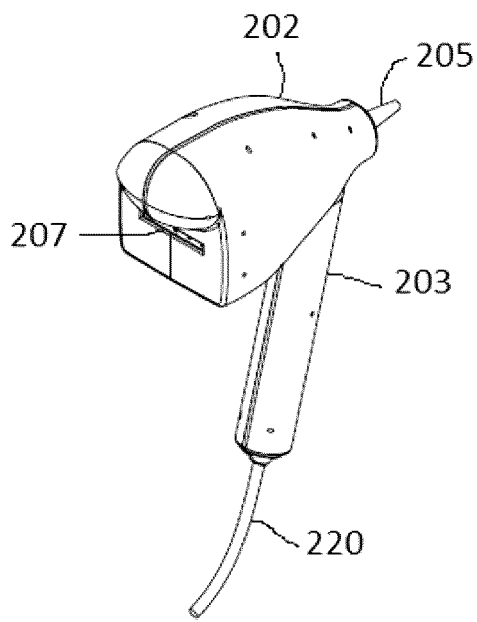
Figure 2D:
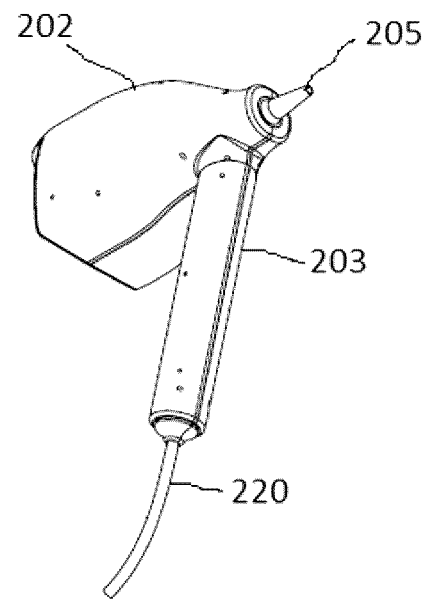
Figure 3A:
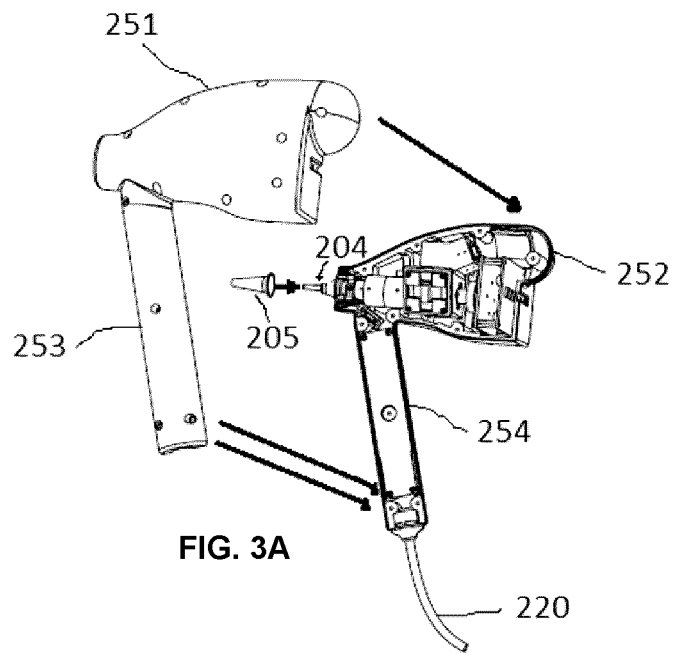
FIG. 3A shows an exploded view of an ear imaging device housing, handle, and speculum assembly.
Figure 3B:
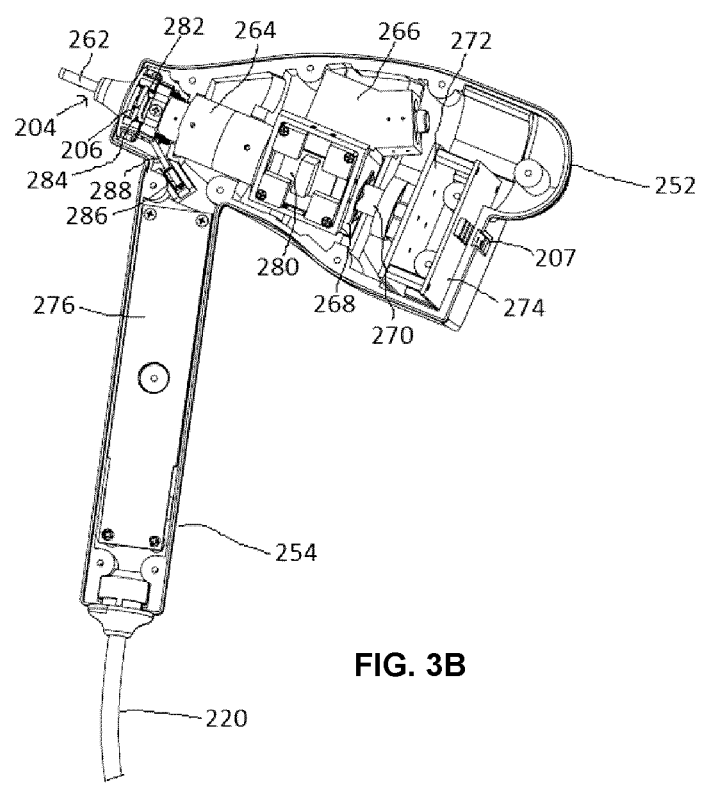
FIG. 3B shows a view of the interior of an ear imaging device.

In FIG. 1B, a window 150 on a computer display for an ear imaging system in Doppler mode displays status indicators 152, user instructions 154, program menu 156, and mode command buttons 158. An infrared camera image 160 displaying the tympanic membrane and middle ear of a subject has an overlaid diagonal line 164 across the infrared image that illustrating the slice selected for showing in B-mode. The B-mode image 162 is overlaid with depth selection indicators 166 as upper and lower horizontal lines across the B-mode image, illustrating the depth selected for imaging. At center, a Doppler image 170 is overlaid with Doppler selection indicators 172 as left and right vertical lines across the Doppler image, containing a region with vibration displacement amplitude information in false color. The false color is interpreted by the user with assistance from the color legend 174.

This large number of features and functions means that a user interface preferably allows for the user to operate at least the basic functions of the imaging system, more preferably more than the basic functions, still more preferably without the need of an additional user, and even still more preferably while holding the imaging device within the subject's ear canal in proper position for imaging.

The present inventors, in designing a handheld imaging diagnostic device configured for the vibrometric data, also found that such a device can be very sensitive to vibrations and other mechanical perturbations during the diagnostic procedure. For example, in middle ear OCT Doppler vibrometry, the vibration amplitude and phase of middle ear structures is determined by interferometrically measuring the change in the optical phase of light reflected from those structure over time. When applied to middle ear diagnostics, OCT Doppler vibrometry can be made sensitive to vibrations smaller than 1 nm, with vibration amplitudes ranging from 10 pm to 10 microns. Measurements are typically made over a frequency range from 20 Hz to 20 KHz, although for some applications such as animal imaging, the upper end of the range may extend to 40 KHz or 100 KHz.

In order to take advantage of this high sensitivity to vibration, the present inventors found that it can be important that the mechanics and ergonomics of the OCT system are compatible with and/or facilitate a high degree of mechanical stability during measurement. In particular, when attempting to control acquisition of vibrometric data of the inner ear using a handheld vibrometric diagnostic device using optical coherence tomography as a detection modality, the present inventors found that motion of the operator can have an impact on the quality of the recorded vibrometric data. For example, the present inventors found that incorporating input mechanisms, such as buttons, onto the handheld vibrometric diagnostic device was problematic because the actuation of the input mechanism would mechanically perturb the device and reduce the quality of the collected vibrometric data. Indeed, traditional video otoscope designs that incorporate buttons onto a handpiece that is inserted into the ear are unable to achieve a high degree of stability because pressing buttons in order to activate the functions of the imaging system inevitably causes motion of the otoscope. The present inventors also found that when an operator attempted to control the acquisition of vibrometric data from a handheld vibrometric diagnostic probe by interacting with a desktop console connected to the handheld vibrometric diagnostic probe, the motion of the operator when interacting with the console also resulted in impaired vibrometric data quality. The present inventors recognized that it remains desirable to perform OCT Doppler vibrometry using an imaging handpiece with a form factor similar to an otoscope, because this is a form factor that is familiar and intuitive to clinicians, because this form factor is conducive to being held very stably in the ear by a clinician who uses his fingers to brace against the patient's head and because the form factor readily allows for the incorporation of a speaker at the distal end which is a requirement for Doppler OCT vibrometry. The present inventors thus sought out to solve the aforementioned technical problems and develop solutions that would allow the user to control an OCT Doppler vibrometry system without needing to press buttons located on the handpiece.

Diagnostic System with Dual Handheld Devices

In order to address the aforementioned problems associated with the need to control a handheld vibrometric diagnostic device without impairing its performance, and the need to control complex user interface features during a diagnostic procedure, the present inventors sought to develop solutions that would facilitate the ability of an operator to provide input for controlling the operation of a handheld vibrometric diagnostic device while avoiding disruption to the device during its operation. It was found that this problem could be solved by providing a system that includes a handheld vibrometric diagnostic device (e.g. designed for insertion into the ear canal) and a separate handheld controller designed for use in the opposite hand from the one holding the handheld vibrometric diagnostic device, with the handheld controller incorporating an input receiving mechanism, such as a set of buttons, that allows the system to be controlled without causing mechanical motion of the handheld vibrometric diagnostic device.

In some example embodiments, the handheld controller is configured such that some or all of the fingers of the hand holding the handheld controller are permitted to be free in order to allow them to be useful during a diagnostic procedure, such as in the case of vibrometric measurements of the ear, in which it can be beneficial to hold and pull on the pinna in order to straighten the ear canal and to ease insertion of the handheld vibrometric diagnostic device into the ear canal.

Various example embodiments of the present disclosure thus provide systems and method in which a handheld controller that is physically distinct and separate from the handheld vibrometric diagnostic device, is employed to control one or more aspects of the operation of the handheld vibrometric diagnostic device during its use, and/or to control one or more features of a user interface associated with the handheld vibrometric diagnostic device. A dual-handheld system is therefore provided that includes both a handheld vibrometric diagnostic device and an associated handheld controller, such that the operator may hold the handheld vibrometric diagnostic device in their dominant hand and also hold the handheld controller in the nondominant hand, or vice versa if that is the preference of the operator.

As noted above, the handheld controller may include an input receiving mechanism (various examples of which are described below), and the handheld controller may be configured such that when it is held in a second hand of an operator (with the handheld vibrometric diagnostic device supported in an operative position relative to a patient with a first hand of the operator), the input receiving mechanism is capable of being actuated by a digit of the second hand while maintaining support of the handheld controller by the second hand, in the absence of contact with the handheld imaging device. Such an example embodiment facilitates control of the handheld imaging device without mechanically perturbing the handheld imaging device.

In some example embodiments, the handheld vibrometric diagnostic device includes a distal portion that is configured to contact a patient and/or be inserted into an opening, orifice, lumen or incision of a patient. For example, in some example embodiments described in detail below, the handheld vibrometric diagnostic device is configured for performing vibrometric measures of the human ear. In such an example embodiment, the operator would insert the handheld vibrometric diagnostic device into the patient's ear. The operator would then press buttons on the handheld controller in the non-dominant hand to control one or more of the handheld vibrometric diagnostic device and a user interface associated with the handheld vibrometric diagnostic device (displayed, for example, on a monitor visible to the operator).

The control of the handheld vibrometric diagnostic device and/or user interface may be facilitated by input signals sent from the handheld controller to an intermediate control and processing console (described in further detail below) that is operatively connected to the handheld vibrometric diagnostic device. The control and processing console may be configured to receive the input signals from the handheld controller and control one or both of the handheld vibrometric diagnostic device and a user interface according to the input signals. For example, the control and processing console may send control signals to the handheld vibrometric diagnostic device based on the input signals received from the handheld controller.

Figure 6:
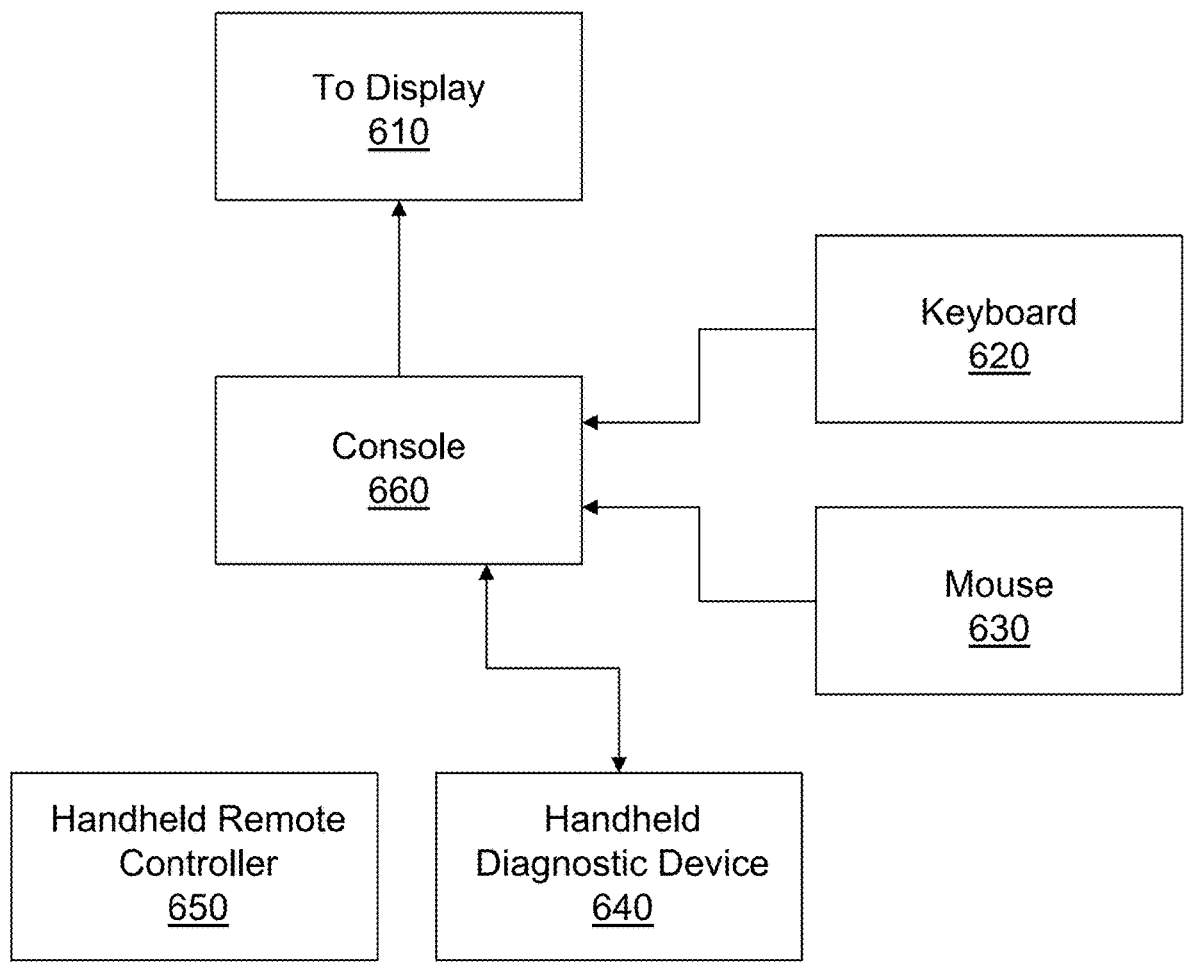
FIG. 6 shows a block diagram of an ear imaging system.

An example embodiment of a diagnostic system that is configured for the measurement of both vibrometric data and imaging data involving the ear, is illustrated in block diagram 600 at FIG. 6. A remote handheld controller 650 held in one hand and a handheld diagnostic device 640 held in the other hand are operatively connected via wireless or wired communication to a console 660 equipped with keyboard 620, mouse 630, and interfacing to a display 610. In some embodiments, the remote controller 650 and the handheld diagnostic device 640 are connected by Bluetooth wireless technology to the control and processing console 660.

Handheld Diagnostic Vibrometric Device

In some example embodiments, the handheld vibrometric diagnostic device may be configured for obtaining vibrometric data alone, or for obtaining vibrometric data in addition to data associated with another diagnostic modality, such as imaging. For example, the handheld vibrometric diagnostic device may be configured for the collection of both imaging data and vibrometric data. An example embodiment of a handheld imaging and vibrometric device 200 is shown in FIGS. 2A-2D and 3A-3B, which operates according to an optical interferometric modality for imaging and vibrometry. In some embodiments, such principles are consistent with PS-OCT as articulated in International Patent Publication WO/2018/152632, hereby incorporated by reference. In some embodiments, such principles are consistent with SS-OCT as articulated in International Patent Publication WO/2017/063090, which is hereby incorporated by reference in its entirety.

As shown in FIGS. 2A-2D and 3A-3B, the example handheld imaging and vibrometric diagnostic device includes an OCT imaging head which is housed within a device housing 202 having a top half 251 and a bottom half 252. The housing 202 is attached to (and may be integral with) a handle 203 having a top half 253 and a bottom half 254, the handle 203 shaped so as to be comfortably held in the hand of a user (e.g., a clinician or medical professional). Protruding from the front of the housing 202 is a speculum holder 204, containing objective optics 262, upon which a removable speculum tip 205 is installed for disposable use in an ear of a subject (e.g., a patient). The speculum holder contains embedded sound tubes to connect the microphone and speaker to the open cavity of the speculum and ear canal. The speculum holder is made of an optically transparent material that allows efficient transmission of the illumination and diffuses the light to a uniform illumination emission pattern. Inside the housing 202 and handle 203 mounted upon the respective bottom halves 252, 254 is an optics and electronics compartment with appropriate optics (relay optics 264, collimation optics 266, dichroic optics 268, camera optics 270), electronics (camera electronics 272, handpiece indicator circuit board 274, handpiece controller circuit board 276, scanning mirror 280), and other elements desirable or necessary for an OCT ear imaging device (thermal regulation 282, camera illumination 206, microphone 284, speaker 206, a speaker tube 288 run within the housing connecting speaker and speculum holder). Protruding from the bottom of the handle 203 is a cable 220 to connect the ear imaging device 200 back to a console with a computer having a display for showing images, the state of the user interface, and other clinically relevant information. A panel of indicator(s) 207 integrated upon the handpiece indicator circuit board 274 may be situated upon the back of the ear imaging device 200 such that the indicator(s) 207 are visible to the user; the indicator(s) can provide some summary information as to operation.

Figure 7:
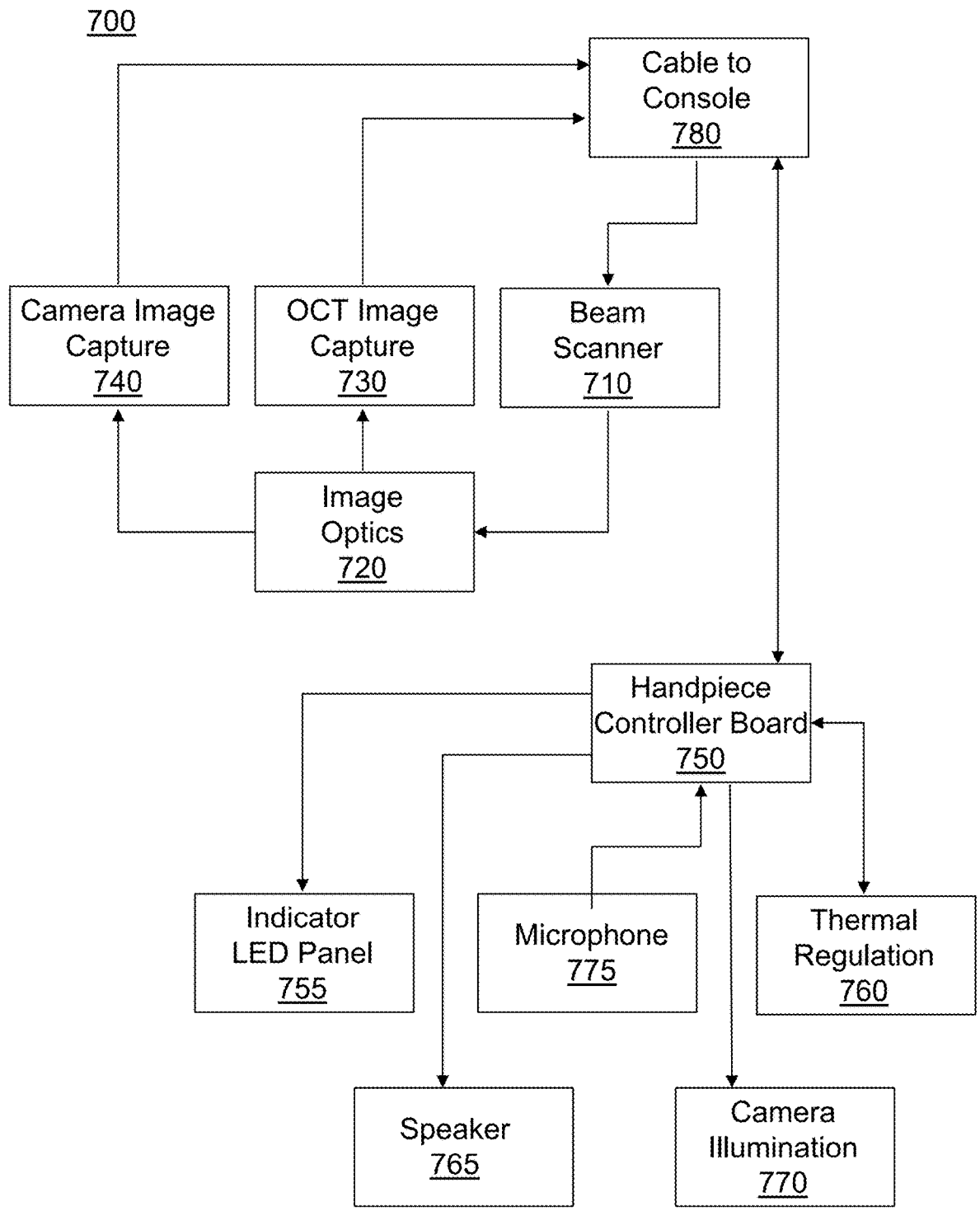
FIG. 7 shows a block diagram of a handheld imaging device.

A block diagram illustrating the components and function of an example embodiment of a handheld imaging device is illustrated at 700 in FIG. 7. A beam scanner 710 is commanded to begin scanning via the console interface 780, which in some embodiments has been indirectly triggered by the handheld remote controller. In some embodiments, the interface to the console 780 is wired, e.g., via fibre optic cable. The scanning OCT beam is processed through image optics 720, the output of which is captured as an OCT image at 730 and co-registered with an en face camera image at 740. These images are then relayed via the interface 780 back to the console for display, annotation, analysis, or storage. The imaging device also has a controller board 750 to support the collection of OCT and camera images. The controller board 750 is in communication with a thermal regulator 760 to keep the objective lens above the dew point in the humid environment of the ear. The board 750 also drives a light source that provides illumination for camera imaging 770. In some embodiments an illumination source provides visible light illumination, e.g., in the wavelength range from 400 nm to 700 nm. In a preferred embodiment, an illumination source provides infrared light illumination, e.g., in the spectral wavelength range from 700 nm to 2000 nm. The board 750 also contains a speaker 765 and microphone 775 for acoustic stimulus. and readout, respectively; and one or more indicators, which can be indicia of controller mode, quality of image taken, status of the console, low battery of the device, or any number of other indicia as programmed. In a preferred embodiment, the indicators are visual indicia displayed upon the handheld imaging device for easy reference by a user. In some embodiments, the indicators are one or more light emitting diodes displayed in a panel. In some embodiments, the indicators indicate sound on/off, laser on/off, illumination on/off, handpiece power on/off, error status, or combinations thereof.

OCT Doppler vibrometry data is produced through the analysis of the interferometrically-measured optical phase at each depth in the sample. For each line in the image, complex A-line data is constructed from the measured data. For the different types of OCT this is done in different ways. In time-domain OCT, the complex A-line data is constructed by measuring the intensity of the interference signal as a delay is introduced into the reference arm and measuring the time-dependent instantaneous phase, e.g. by performing a Hilbert transform on the data. For swept-source OCT and spectral domain OCT, the complex A-line is obtained as the complex Fourier transform of the measured spectrogram, either as a function of time in the case of swept-source OCT or of detector location in the case of spectral domain OCT. When the tissue is moving due to excitation by a mechanical stimulus such as a sound source, the phase of each pixel in the A-line will be perturbed by the motion such that a phase shift $$\phi = 4\pi \frac{\Delta x}{\lambda}$$

is introduced by a sound induced displacement $\Delta x$ where $\lambda$ is the optical wavelength. If the stimulus is a pure tone, then the displacement will be sinusoidal and may be analyzed by performing spectral analysis on the optical phase, e.g. by taking a Fourier transform or by performing lock-in detection. This type of analysis results in the determination of the amplitude and phase of the displacement at each pixel location in response to the stimulus.

Handheld Controller

In some example embodiments, the handheld controller is configured such that an operator (e.g. clinician) can access and/or control, via the handheld controller, at least some functions of the handheld vibrometric diagnostic device, and/or at least some functions of a user interface, while sitting or otherwise residing next to the patient, while one of the clinician's hands holds the handheld vibrometric diagnostic device in an operative position (e.g. such that a distal region of the device is inserted in the patient's ear canal in the case of a handheld vibrometric diagnostic device for imaging the ear). As described in further detail below, various example embodiments of the present disclosure enable a single operator to interact with a vibrometric system involving insertion of a distal region of a handheld vibrometric diagnostic device into the ear canal of a patient, in such a way that the dominant hand of the operator may hold the handheld vibrometric diagnostic device without the need to otherwise interact with (e.g. press buttons located on) the handheld vibrometric diagnostic device. As described below, various example systems include, in addition to a handheld vibrometric diagnostic device having an otoscopic form factor, a handheld controller that facilitates interaction with, and control of, a user interface of the diagnostic system.

In some example embodiments, the handheld controller includes a a support configured to contact the hand that supports the handheld controller during its operative use (hereafter referred to as the "second hand", the first hand being understood as supporting the handheld vibrometric diagnostic device during the diagnostic procedure) such that the weight of the handheld controller is at least partially supported while permitting use of at least two digits of the second hand. Various examples of such a support (e.g. support feature, support mechanism) are described below.

For example, the handheld controller may include a support surface positioned to contact an upper portion of the second hand of the operator during use of the handheld controller, such that at least a portion of the weight of the handheld controller is supported. An example implementation of such an embodiment is shown in FIGS. 4A-4C and FIG. 5. The handheld controller 400 includes a controller housing 402 shaped so as to have an ergonomic top surface 404 and a support ledge 420 and is fabricated so as to receive a removable battery compartment lid 411 and a removable circuit board compartment lid 415. The support ledge 420 is molded so as to support the weight of the controller by contact with the operator's hand, freeing the fingers and thumb to manipulate the subject's pinna.

In another example embodiment, the handheld controller includes a strap configured to support the handheld controller relative to the second hand. An example implementation of such an embodiment is illustrated in FIGS. 4D-4G, where a support strap 450 is shown integrated with the handheld controller.

Figure 4D:
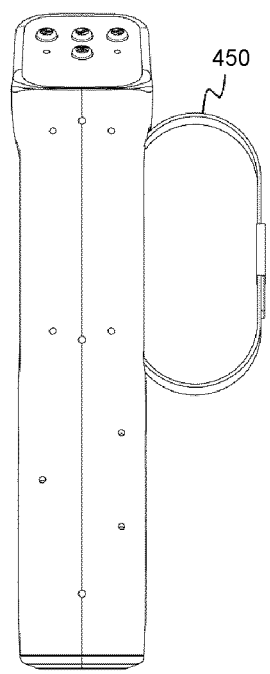
FIGS. 4D-4G illustrate an alternative example handheld controller including a support strap.
Figure 4E:
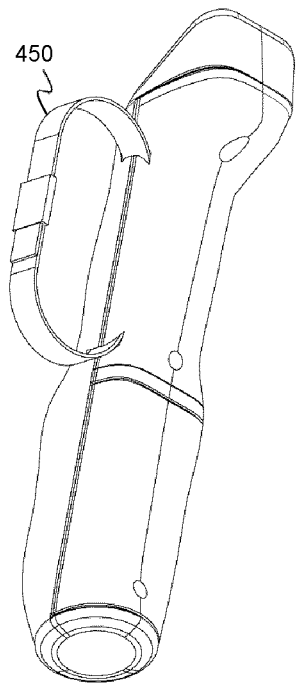
Figure 4F:
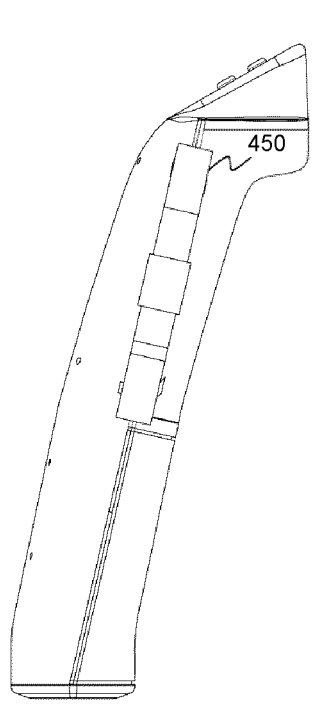
Figure 4G:
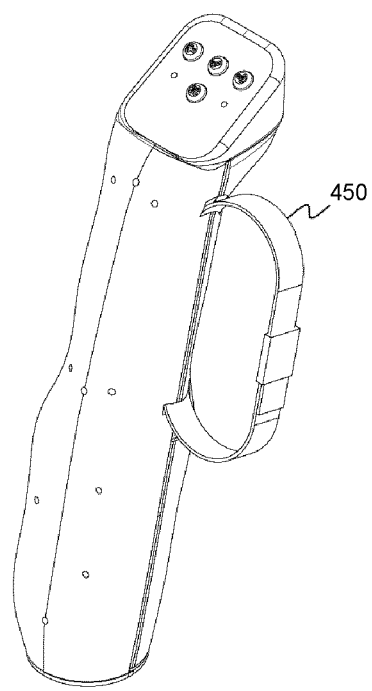
Figure 4H:
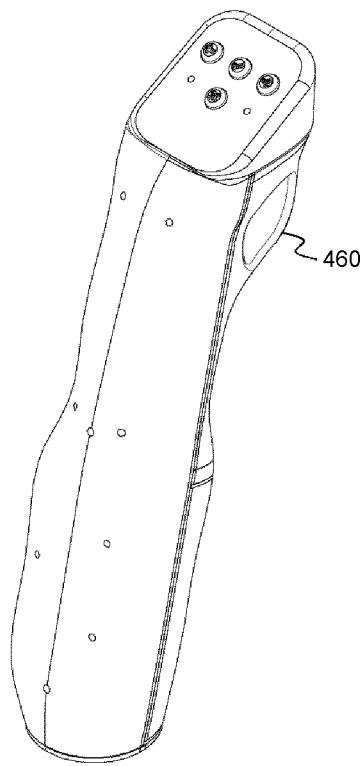
FIGS. 4H-4J illustrate an alternative example handheld controller including a support ring.
Figure 4I:
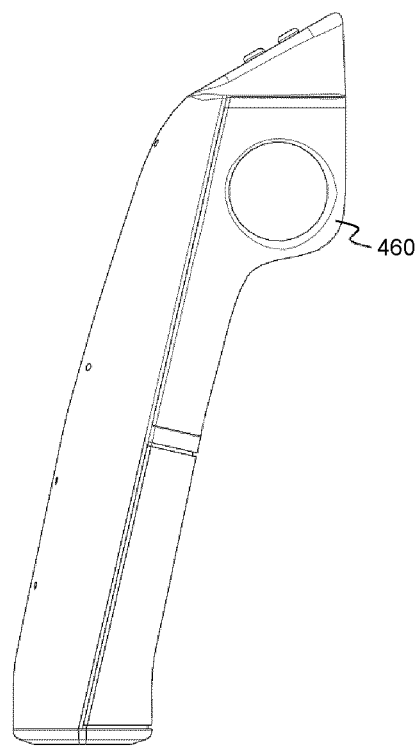
Figure 4J:
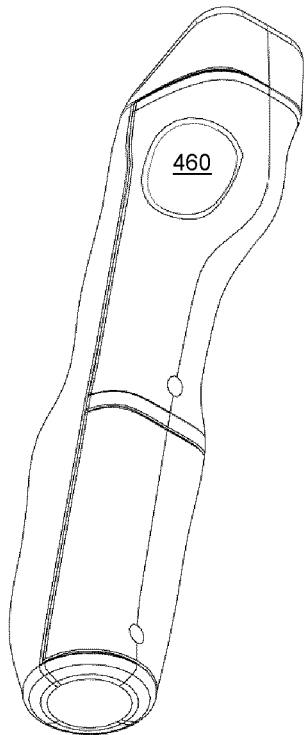
Figure 5:
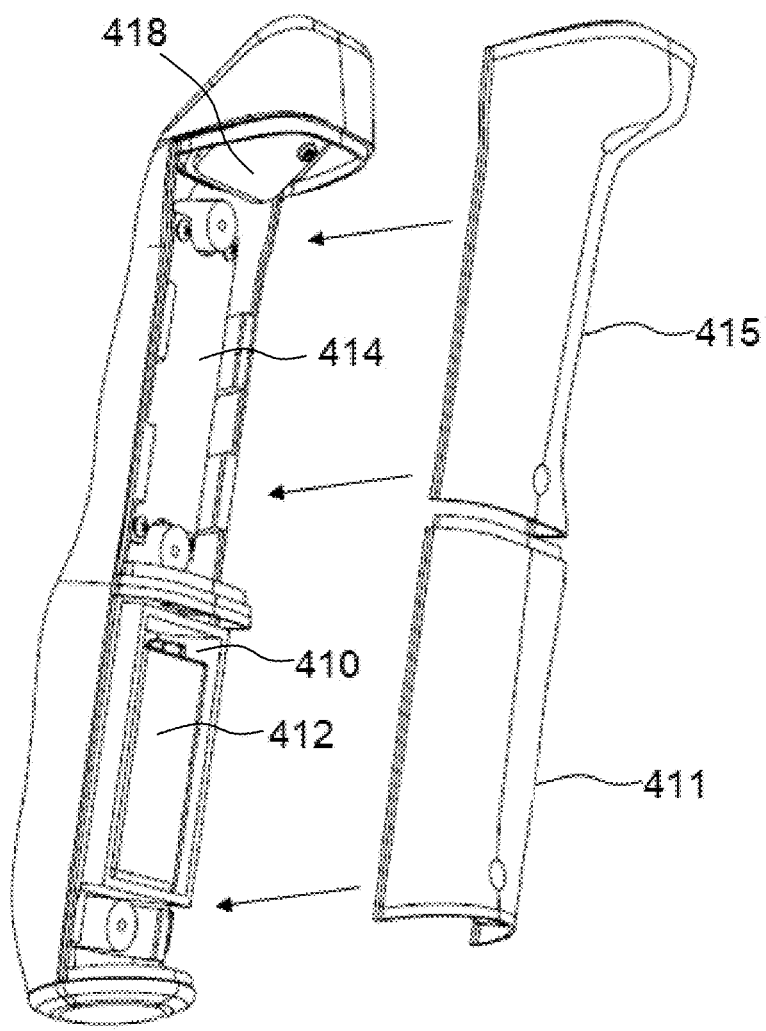
FIG. 5 shows an exploded view of the interior of a handheld remote controller.

In yet another example embodiment, the handheld controller includes one or more rings (full or partial), each ring being configured to receive a respective digit of the second hand. An example implementation of such an embodiment is illustrated in FIGS. 4H-4J, where a support ring 460 is shown integrated with the handheld controller.

In still another example embodiment, the handheld controller includes at least a portion of a glove, the glove being integrated with the handheld controller for supporting the handheld controller while permitting use of the at least two digits when the glove is worn on the second hand As shown in FIGS. 4A-4J, the handheld controller includes an input mechanism for receiving input from a digit of a hand of an operator during use, while the handheld controller is supported. In the example implementations shown, a surface of the handheld controller, such as the top surface, has one or more actuation devices (e.g. buttons) 406 disposed thereon or recessed therein. In some example implementations, a surface of the handheld housing supports one or more indicator light(s) 408. The buttons 406 (and light(s) 408 if equipped) are connected to a user button circuit board 418 found within the top of the controller. The printed circuit board 414 and battery compartment 410 are located inside the controller housing 402 at a position corresponding to their respective lids. The battery compartment 410 is designed to house a battery 412 to power the controller 400.

As noted above, the handheld controller can be connected to a processing and control housing through a wired or wireless configuration. A wireless configuration may be beneficial such that the handheld controller is absent of a physical connection to the control and processing console, in order to avoid transmission of mechanical vibrations to the handheld imaging device from the control and processing console during a diagnostic procedure.

For example, in some example embodiments, the printed circuit board 414 incorporates a transmitter (e.g., a wireless transceiver) and circuitry to electrically connect to the battery 412 and the user button circuit board 418. In some embodiments, the transmitting system transmits whenever a button is pressed. In some embodiments, the transmitting system transmits whenever a button is released. In some embodiments, the transmitting system periodically or upon a state change transmits the on/off status of each button. Transmission may be to, e.g., a computer with a display controlling the console of an imaging system. In some example embodiments, the handheld controller is symmetric so that it can be used equally easily with either the left or right hand.

As noted above, the handheld controller includes an input-receiving means or mechanism configured to actuated by one or more digits of the hand supporting the handheld controller. Non-limiting examples of a suitable input receiving means include buttons, switches, capacitive-based sensors, touchscreen devices, and touchpad devices. In some example implementations, the handheld controller includes a trigger. In some example implementations, the handheld controller communicates with the system through a wireless interface. In some example implementations, the handheld controller communicates with the system through a wired interface. In some embodiments, the handheld controller is configured to control (e.g. drive) the user interface through selectable functions such as, but not limited to, select, back, scroll left/up, and scroll right/down functions.

Figure 8:
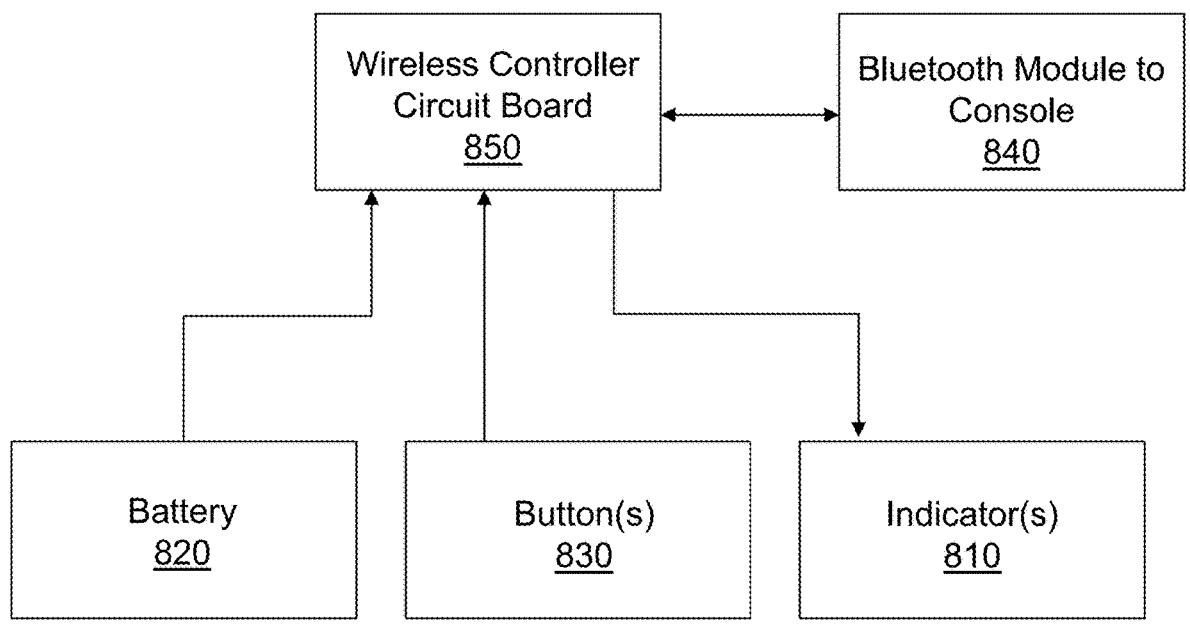
FIG. 8 shows a block diagram of a handheld remote controller.

An example embodiment of a handheld remote controller is illustrated in block diagram 800 at FIG. 8. A controller circuit board 850 is powered by a battery 820, such as a 9V battery, and operatively connected, e.g., wirelessly via Bluetooth Low Energy link, to a control and processing console. The board 850 is also responsive to one or more buttons 830 activated by the user. In some embodiments, the board 850 is responsive to the activation of one button 830. In some embodiments, the board 850 is responsive to two buttons 830. In some embodiments, the board 850 is responsive to three buttons 830. In some embodiments, the board 850 is responsive to four or more buttons 830. In some embodiments, the board 850 is responsive to the activation of combinations of buttons 830 being pressed simultaneously, if any. In some embodiments, the board 850 can recognize the duration held of any or all buttons 830. The board 850 interfaces with one or more indicators 810, which can be indicia of controller mode, quality of image taken, status of the connection to the control and processing console, low battery of the controller, current imaging mode, laser on indicator, sound on indicator or any number of other indicia as programmed. In a preferred embodiment, the indicators 810 are visual indicia displayed upon the handheld remote controller to inform the user about system state. In some embodiments, the one or more indicators 810 are one or more light emitting diodes displayed in a panel.

Figure 9A:
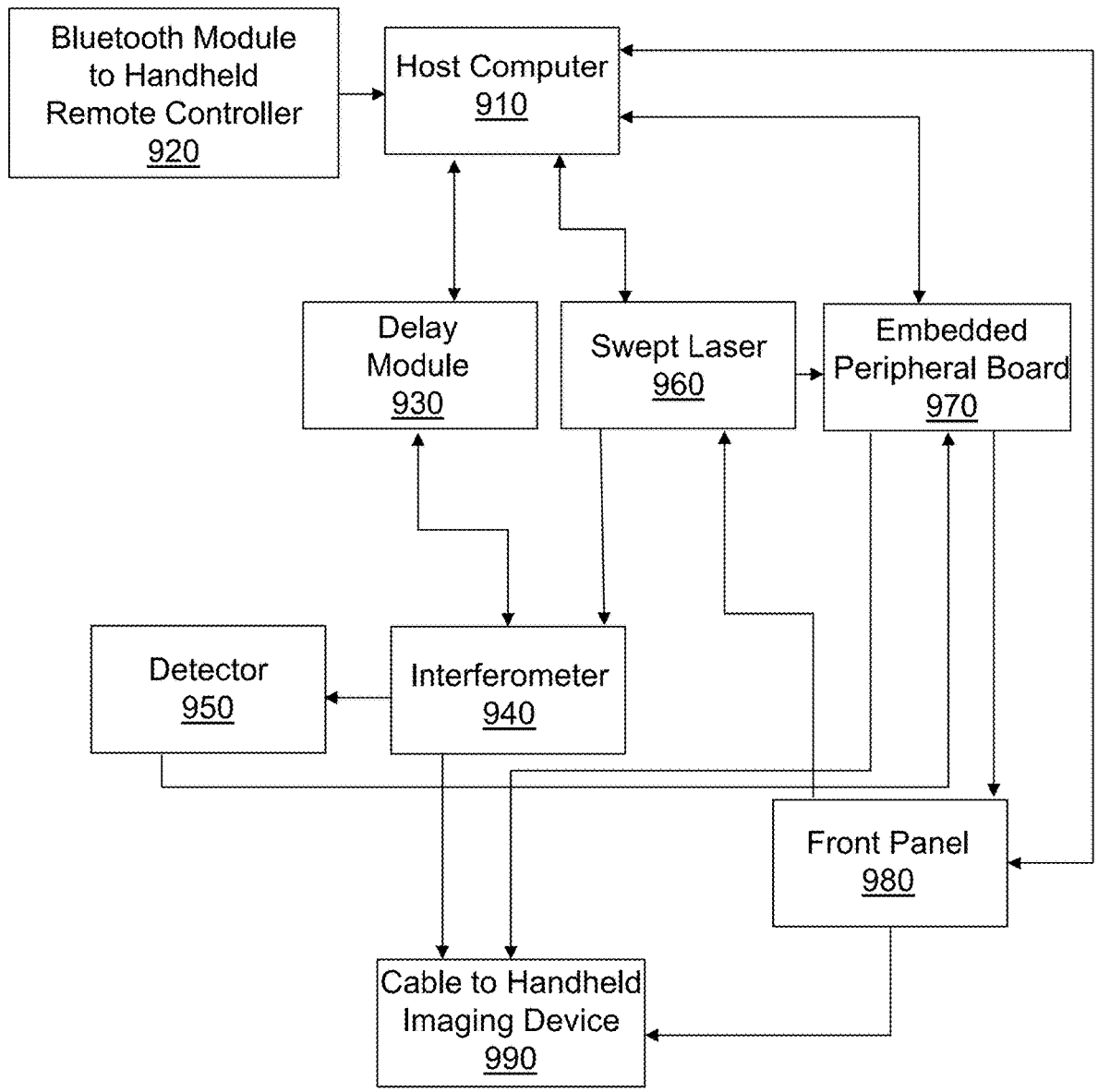
FIG. 9A shows a block diagram of an ear imaging system console.

An example embodiment of a control and processing console for use in an ear imaging system operating on OCT principles is illustrated in block diagram 900 at FIG. 9A. A host computer 910 receives commands from a remote controller 920 that is operatively connected, e.g., by wireless Bluetooth bidirectional link. In some embodiments, the host computer 910 includes one or more processors, memory, storage, and circuitry to interface with peripherals such as delay module 930, swept laser 960, peripheral board 970; to drive one or more displays for display of a graphical user interface or of indicia such as front panel 980; to perform analysis of images; and other capabilities consistent with an ear imaging system. The host computer 910 controls a swept laser 960 which feeds into an interferometer 940 which in turn feeds to a detector 950 whose output flows to the peripheral board 970. The host computer 910 is also in communication with a delay module 930 which controls the delay in one arm of the interferometer 940 to shift the image window axially. In some embodiments, user input from the front panel 980 commands the host computer 910. In some embodiments, user input from the front panel 980 directly addresses the swept laser 960 via a safety interlock driven, e.g., by the position of a key. Input from the laser 960, detector 950, interferometer 940, front panel 980, and peripheral board 970 is consolidated into the wired interface to the imaging device 990.

Figure 9B:
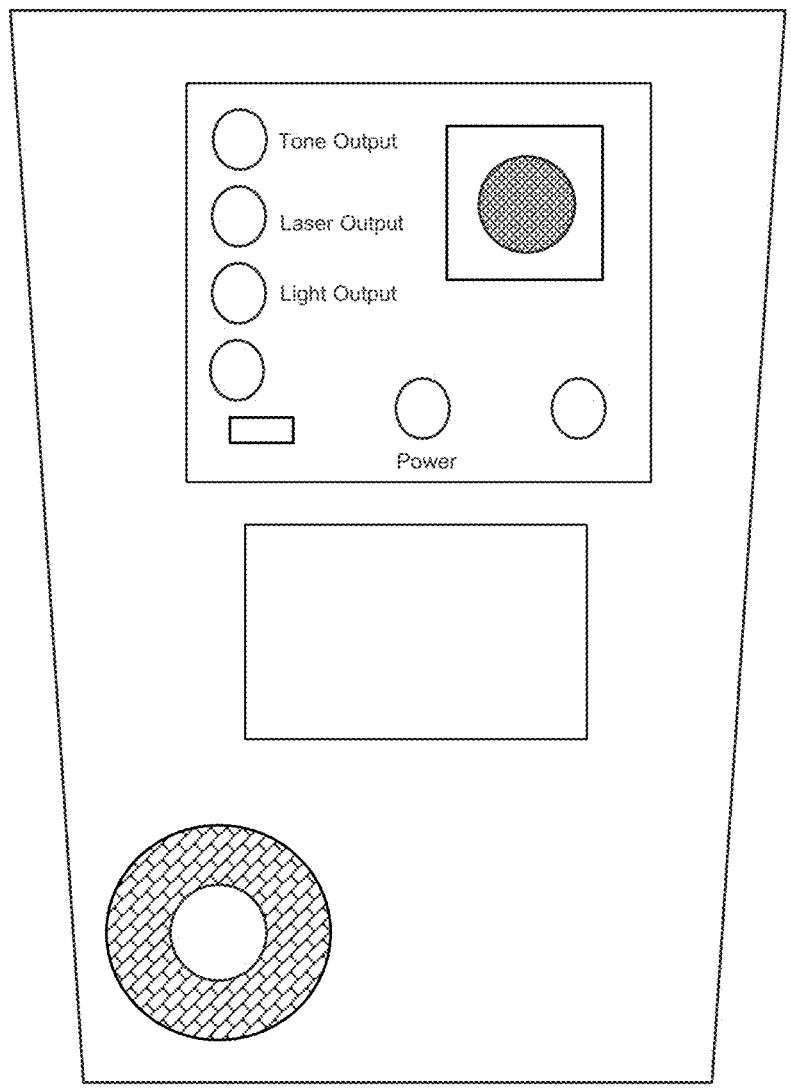
FIG. 9B shows a depiction of an ear imaging system console front panel.

In some embodiments, the front panel 980 displays one or more of the elements depicted in FIG. 9B, including power switch, laser output indicator, sound output indicator, and illumination output indicator etc. In some embodiments, the front panel 980 provides USB port; console power button; laser interlock key; indicator LEDs indicating the respective on/off status of sound, laser, or illumination; speaker; interconnect point for cabling entering the control and processing console; or combinations thereof.

Although the preceding example embodiments have been disclosed within the example context of vibrometric systems and devices, it will be understood that various other configurations of a system involving a handheld device and handheld controller may be provided according the present disclosure. For example, in some example embodiments, the handheld diagnostic device may be configured for imaging in the absence of the collection of vibrometric data. In other example embodiments, the handheld device that is employed during the medical procedure, and which may be controlled by the handheld controller, may be a therapeutic device, or a combined therapeutic and diagnostic device. Non-limiting examples of handheld therapeutic devices include drills, therapeutic laser, high intensity focused ultrasound transducer, radio-frequency ablation element, cryogenic element, heating element, blade, suction device, curette, scissors, bur, saw, rongeur, grasper, forceps. retractor, distractor, irrigation or injection needle and sonotrode.

Moreover, while some example embodiments pertain to the use of a handheld diagnostic device that is configured for insertion into the body (or into an orifice of the body), other example embodiments may employ a handheld diagnostic device, vibrometric or imaging or both, that is configured to obtain measurements of the body in a non-contact configuration.

Example Workflow

In systems having a controller and an imaging device, the controller can be held in one of several positions one-handedly, leaving the other hand free to hold the imaging device in one of several positions. Example positions are described below. In some embodiments, a handheld remote controller is held in the one hand of a user while simultaneously pulling the pinna of a subject to straighten the ear canal. In some embodiments, the handheld remote controller's buttons are pressable by the user while simultaneously pulling the pinna of a subject. In some embodiments, the other hand of the user also holds an OCT handheld ear imaging device that is inserted in the subject's ear.

Figure 12A:
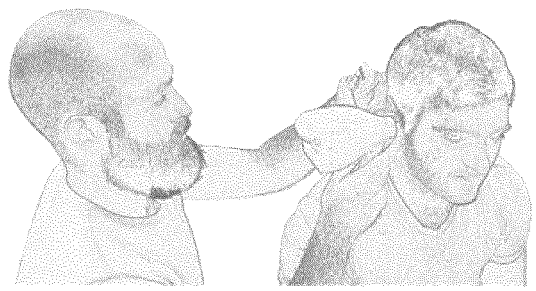
FIGS. 12A-12C show photographs of a wireless handheld controller held in a user's left hand while also holding a subject's inferior right ear and a user's right hand using an ear imaging device in the subject's ear.
Figure 12B:
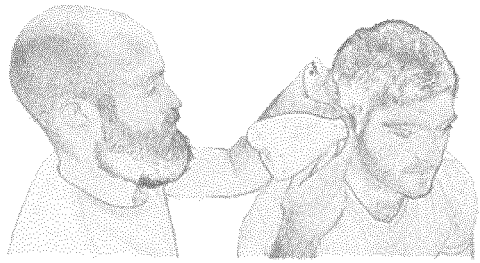
Figure 12C:
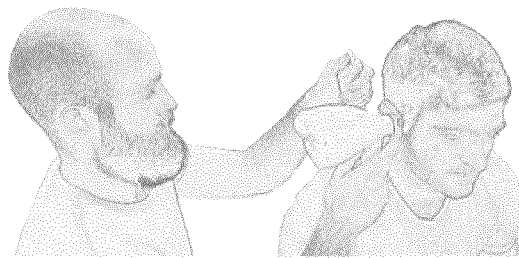
Figure 12D:
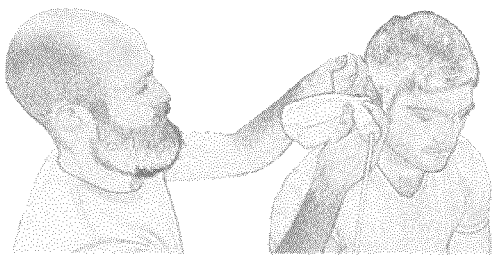
FIGS. 12D-12F show photographs of a wireless handheld controller held in a user's left hand and a user's right hand using an ear imaging device with the handle in a superior-anterior orientation in a subject's ear while holding the subject's right ear.
Figure 12E:
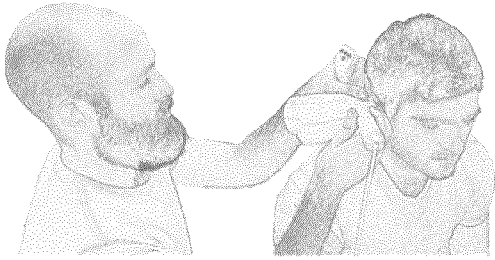
Figure 12F:
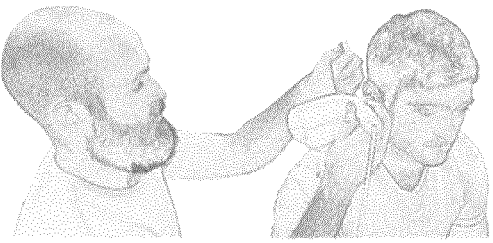

Referring now to FIGS. 12A-12C, an example method of use of a diagnostic system according to the present disclosure is illustrated for a diagnostic procedure involving the ear. As shown in the figures, a handheld diagnostic device (e.g. a handheld OCT-based vibrometric ear imaging device), having a distal region suitable for insertion within the ear, is held by a first hand of an operator, with the handle pointing in an inferior direction while the operator's fingers hold the handheld diagnostic device around its handle. FIGS. 12D-12F shown an alternative configuration for holding the handheld diagnostic device, in which the operator holds the handheld diagnostic device, in the first hand, with the handle pointing in the superior-anterior or superior-posterior directions as desired. The handheld controller is held by the second hand of the operator.

As shown in FIGS. 12A and 12D, the distal portion of the handheld diagnostic device is inserted into the ear after using knuckles of two interior fingers of the second hand (the hand holding the handheld controller) to grip and pull back on a subject's pinna, resting the controller's support ledge on the second hand, and leaving the thumb free to interact with buttons on the controller. The thumb, or another digit, may be employed to initiate a diagnostic measurement after the handheld diagnostic probe is inserted, while avoiding contact between the second hand and the handheld diagnostic device. Alternatively, as shown in FIGS. 12B and 12D, the pinna may be gripped and pulled back by the thumb and an interior finger of the operator's second hand.

Figure 10:
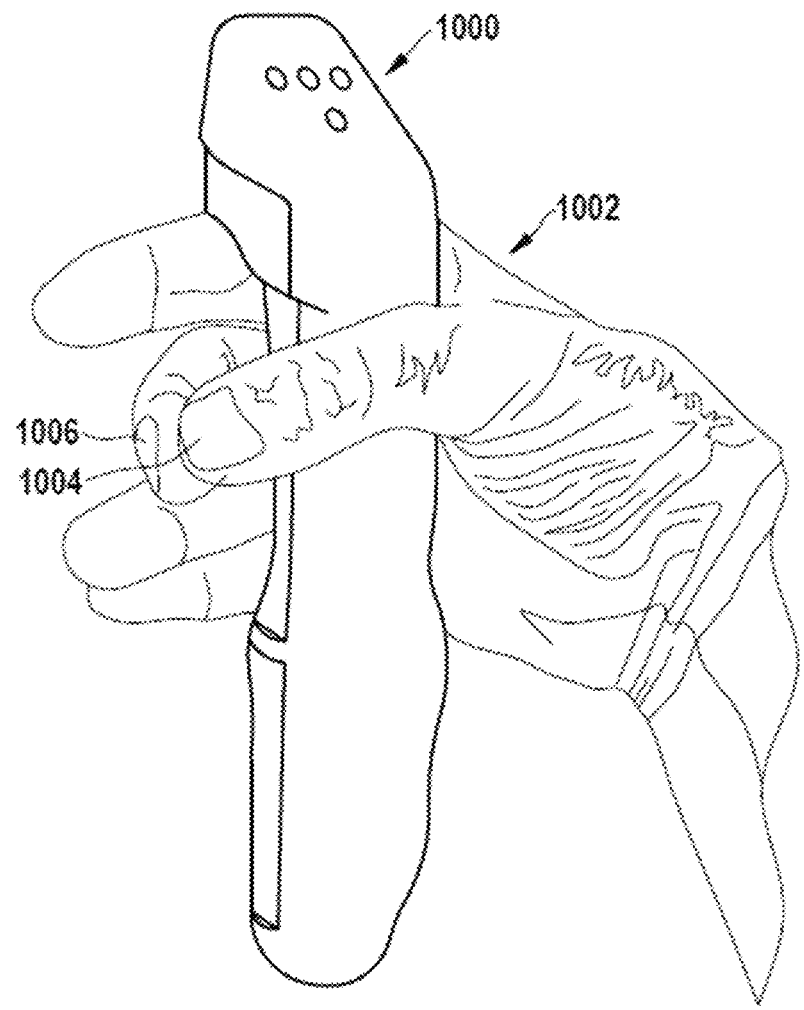
FIG. 10 shows a handheld remote controller being held in the right hand of a user so as to leave fingers available for manipulation of a subject's pinna.
Figure 11:
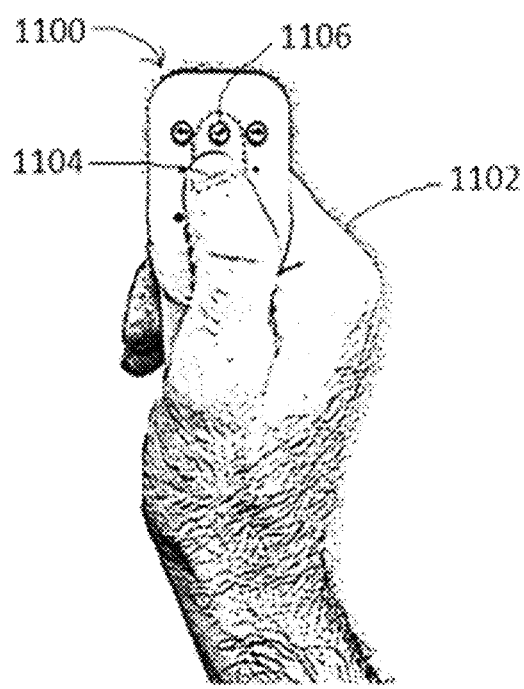
FIG. 11 shows a handheld remote controller being held in the right hand of a user so as to leave thumb available to depress one or more buttons on the top of the controller (action shown in dotted lines).

In some embodiments, the handheld controller 1000 is designed to be held securely in an operator's hand 1002 while leaving the thumb 1004 and another interior finger (e.g., the middle finger 1006) free to grip and pull back on the patient pinna during initial insertion of the speculum. Examples are shown in FIG. 10 and illustrated in use at FIGS. 12B and 12E. In some embodiments, the handheld controller 1100 is designed so as to be gripped in an operator's hand 1102 with the fingers, while the thumb 1104 is free to interact with one or more buttons 1106 on the top face of the controller 1100. This is shown in FIG. 11 and illustrated in use at FIGS. 12C and 12F.

Figure 13:
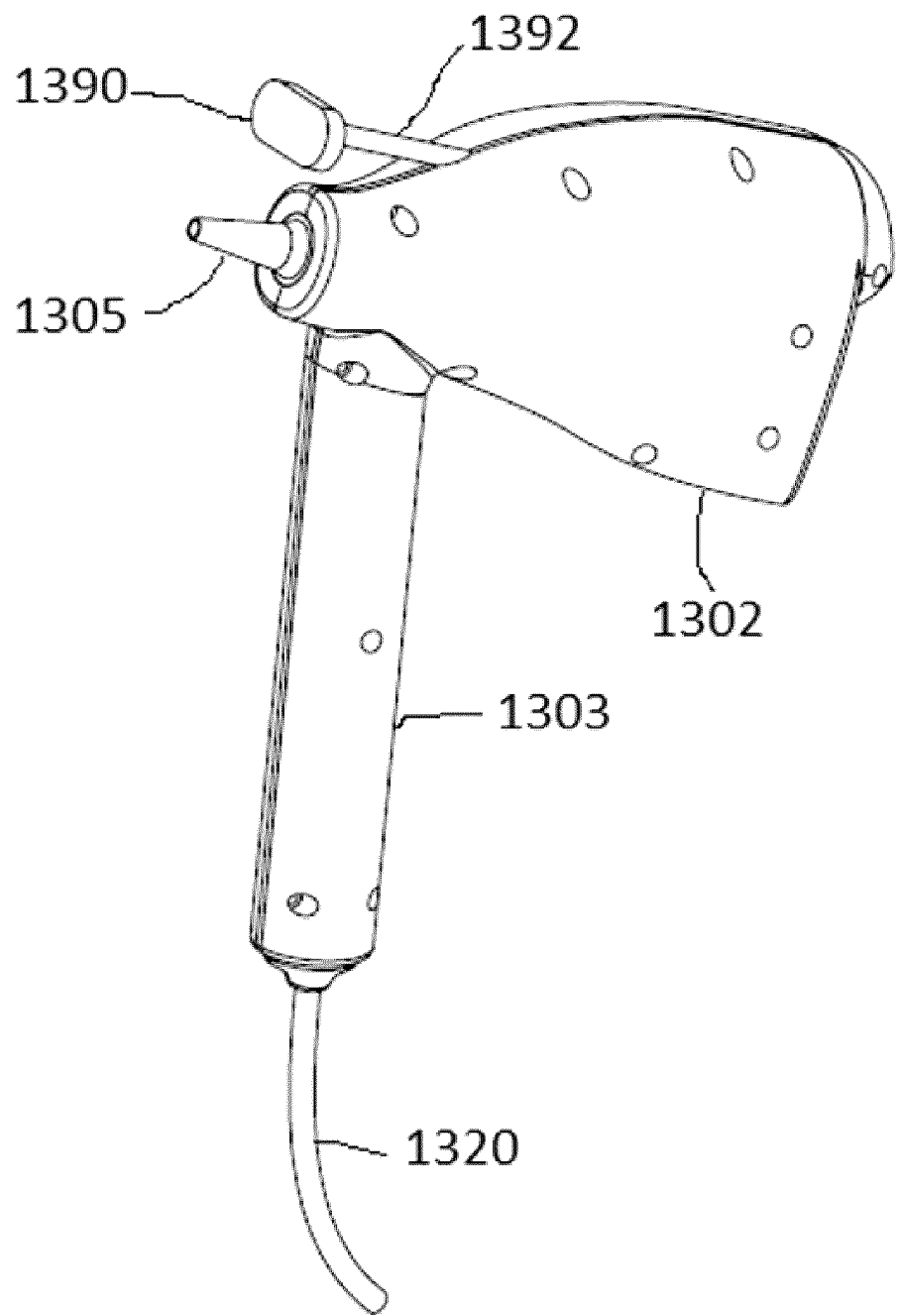
FIG. 13 shows the exterior of a handheld OCT ear imaging device.

Referring to FIG. 13, shown is the exterior of a handheld OCT ear imaging device. Similar to the ear imaging device 200 in FIGS. 2A-2D, the handheld OCT ear imaging device of FIG. 13 includes a device housing 1302 and a handle 1303. A removable speculum tip 1305 is installed for disposable use in an ear of a subject (e.g., a patient). Protruding from the bottom of the handle 1303 is a cable 1320. A stabilization rod 1392 emanates from the device housing 1302. The stabilization rod 1392 includes a terminal element 1390 suitable for placement against a head of the subject for stabilization of said hand held imaging device against motion of the subject during an imaging procedure. The said stabilization rod 1392 is capable of telescoping motion.

While the preceding example method relates to an example diagnostic procedure involving the retraction of the pinna, it will be understood that the example method may be adapted for use with diagnostic and/or therapeutic procedures involving anatomical regions other than the ear, with the retraction of anatomical structures other than the pinna.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A vibrometric diagnostic system for imaging within an ear of a subject, the vibrometric diagnostic system comprising:
a handheld vibrometric diagnostic device comprising a distal region configured for insertion within the ear of the subject during a diagnostic procedure;
a control and processing console operatively connected to said handheld vibrometric diagnostic device, said control and processing console comprising at least one processor and associated memory, said memory comprising instructions executable by said processor for performing operations comprising:
sending control signals to said handheld vibrometric diagnostic device for controlling operations thereof;
processing vibrometric data received from said handheld vibrometric diagnostic device; and
an input receiving mechanism remote from said handheld vibrometric diagnostic device, said input receiving mechanism being operatively coupled to said control and processing console for use in controlling operation of said handheld vibrometric diagnostic device, such that said control signals are dependent on an input signal received by said input receiving mechanism, thereby facilitating control of said handheld vibrometric diagnostic device without mechanically perturbing said handheld vibrometric diagnostic device.

2. The system according to claim 1 wherein said processor is further configured to display, on a display device, in real-time while said handheld vibrometric diagnostic device resides in an operative position with said distal region residing within the ear of the subject, a user interface comprising one or more vibrometric measures; and
wherein said input receiving mechanism is further configured for receiving input from an operator for controlling the user interface in the absence of contact with said control and processing console and said handheld vibrometric diagnostic device, thereby facilitating control of the user interface without mechanically perturbing said handheld vibrometric diagnostic device.

3. The system according to claim 1 wherein said input receiving mechanism comprises a wireless transmitter for transmitting the input signal to said control and processing console, such that said input receiving mechanism is absent of a physical connection to said control and processing console, thereby avoiding transmission of mechanical vibrations to said handheld vibrometric diagnostic device via said control and processing console during the diagnostic procedure.

4. The system according to claim 1 wherein said handheld vibrometric diagnostic device employs an optical imaging modality.

5. The system according to claim 4 wherein said optical imaging modality is optical coherence tomography.

6. The system according to claim 4 wherein said handheld vibrometric diagnostic device further comprises a camera and a light source configured to collect image data in one or more of an infrared and visible spectrum.

7. The system according to claim 1 further comprising a handheld controller operatively connected to said control and processing console, said handheld controller comprising said input receiving mechanism;
said handheld controller being configured such that when said handheld vibrometric diagnostic device is supported by a first hand of an operator and said handheld controller is supported by a second hand of the operator, said input receiving mechanism is capable of being actuated by a digit of the second hand while maintaining support of said handheld controller by the second hand, in the absence of contact with said control and processing console and said handheld vibrometric diagnostic device, thereby facilitating control of said handheld vibrometric diagnostic device without mechanically perturbing said handheld vibrometric diagnostic device.

8. The system according to claim 7 wherein said handheld controller comprises a support configured to contact the second hand during use for at least partially supporting a weight of said handheld controller while permitting use of at least two digits of the second hand.

9. The system according to claim 8 wherein said support comprises a support surface positioned to contact an upper portion of the second hand of the operator during use of said handheld controller, such that at least a portion of the weight of said handheld controller is supported.

10. The system according to claim 8 wherein said support comprises a strap configured to support said handheld controller relative to the second hand.

11. The system according to claim 8 wherein said support comprises one or more rings, each ring being configured to receive a respective digit of the second hand.

12. The system according to claim 8 wherein said support comprises at least a portion of a glove that is integrated with said handheld controller for supporting said handheld controller while permitting use of the at least two digits.

13. The system according to claim 7 wherein said handheld vibrometric diagnostic device and said handheld controller are shaped so as to be interchangeable with respect to which hand the operator employs to hold either device.

14. The system according to claim 1 wherein said distal region of said handheld vibrometric diagnostic device comprises an objective lens, said system further comprising a thermal regulator configured to be controllable by said control and processing console to maintain said objective lens above a dew point within a humid environment of the ear.

15. The system according to claim 1 wherein said handheld vibrometric diagnostic device and said control and processing console are configured to interrogate a middle ear region of the ear via a phase-sensitive optical coherence tomography subsystem, said handheld vibrometric diagnostic device further comprising a camera and a light source, wherein a reference frame of said camera is co-registered with a reference frame of said phase-sensitive optical coherence tomography subsystem, and wherein said control and processing console is further configured to display, on a user interface:
- a structural optical coherence image characterizing one or more structures of the middle ear region;
- a camera image acquired by the camera; and
- an annotation, within the camera image, indicating a region associated with acquisition of structural optical coherence image.

16. The system according to claim 15 wherein the structural optical coherence image is a B-mode image slice and the annotation is a linear annotation.

17. The system according to claim 15 wherein said control and processing console is configured such that the user interface further displays one or more vibrometric measures generated based on the vibrometric data.

18. The system according to claim 15 wherein the annotation is a first annotation and the region is a first region, and wherein said control and processing console is configured to generate, within the structural optical coherence image, one or more additional annotations indicative of a second region associated with acquisition of the vibrometric data.

19. A method of performing a diagnostic procedure involving an ear of a subject, the method comprising:
   providing a system according to claim 1;
   while supporting the handheld vibrometric diagnostic device with a first hand:
      employing at least two digits of a second hand to grip and pull back on a pinna of the ear of the subject;
      inserting the distal region of the handheld vibrometric diagnostic device into the ear of the subject; and
      without contacting the handheld vibrometric diagnostic device with the second hand, actuating the input receiving mechanism to initiate a diagnostic measurement with the handheld vibrometric diagnostic device.

20. The method according to claim 19 wherein the pinna is gripped by knuckles of two interior fingers of the second hand.

21. The method according to claim 19 wherein the pinna is gripped by a thumb and an interior finger of the second hand.

22. The method according to claim 19 wherein the input receiving mechanism is actuated by a thumb.

* * * * *